US008846902B2

(12) United States Patent
O'Connor et al.

(10) Patent No.: US 8,846,902 B2
(45) Date of Patent: Sep. 30, 2014

(54) PROCESS FOR THE CONVERSION OF CELLULOSE IN HYDRATED MOLTEN SALTS

(75) Inventors: Paul O'Connor, Hoevelaken (NL); Jacob Adriaan Moulijn, The Hague (NL); Michiel Makkee, Delft (NL); Sjoerd Daamen, Bocairent (ES); Rafael Menegassi de Almeida, Waalre (NL)

(73) Assignees: BIOeCON International Holding N.V., Hoevelaken (NL); Petróleo Brasileiro S.A.—PETROBRAS, Rio de Janeiro (BR)

( * ) Notice: Subject to any disclaimer, the term of this patent is extended or adjusted under 35 U.S.C. 154(b) by 224 days.

(21) Appl. No.: 12/682,279

(22) PCT Filed: Jun. 24, 2008

(86) PCT No.: PCT/EP2008/058044
§ 371 (c)(1),
(2), (4) Date: Apr. 9, 2010

(87) PCT Pub. No.: WO2009/047023
PCT Pub. Date: Apr. 16, 2009

(65) Prior Publication Data
US 2010/0234586 A1 Sep. 16, 2010

Related U.S. Application Data

(60) Provisional application No. 60/929,373, filed on Oct. 9, 2007.

(51) Int. Cl.
| | | |
|---|---|---|
| C07H 1/06 | (2006.01) | |
| C07H 1/08 | (2006.01) | |
| C13K 1/02 | (2006.01) | |
| C07H 3/02 | (2006.01) | |
| C07H 1/00 | (2006.01) | |
| C08B 1/00 | (2006.01) | |

(52) U.S. Cl.
CPC .. C13K 1/02 (2013.01); C07H 3/02 (2013.01); C07H 1/00 (2013.01); C08B 1/003 (2013.01)
USPC ............... 536/128; 536/124; 127/36; 127/37

(58) Field of Classification Search
CPC ............... C07H 1/06; C07H 1/08; C13K 1/02
USPC ............... 127/37, 36; 536/124, 128
See application file for complete search history.

(56) References Cited

U.S. PATENT DOCUMENTS

| | | |
|---|---|---|
| 1,943,176 A | 1/1934 | Graenacher |
| 4,018,620 A | 4/1977 | Penque |
| 4,452,640 A | 6/1984 | Chen et al. |
| 4,525,218 A | 6/1985 | Chen et al. |
| 4,637,835 A | 1/1987 | Nagle |
| 4,787,939 A | 11/1988 | Barker et al. |
| 4,999,149 A | 3/1991 | Chen |
| 6,824,599 B2 | 11/2004 | Swalotski et al. |

FOREIGN PATENT DOCUMENTS

| | | |
|---|---|---|
| EP | 96497 A2 * | 12/1983 |
| WO | WO 02088057 A1 * | 11/2002 |
| WO | 2005017001 A1 | 2/2005 |
| WO | 2007101812 A1 | 9/2007 |
| WO | 2007138256 A2 | 12/2007 |
| WO | 2008098037 A2 | 8/2008 |

OTHER PUBLICATIONS

Voigt et al. (Pure Appl. Chem., vol. 74, No. 10, pp. 1909-1920, 2002).*
Zhu et al., Green Chem., 2006, 8 325-327.
Swatloski R P et al: "Dissolution of Cellose With Ionic Liquids" Journal of the American Chemical Society,American Chemical Society, Washington,DC.; US, vol. 124, Jan. 1, 2002, p. 4974/4975, XPOOI166990, ISSN: 0002-7863, the whole document.
Anantharam P Dadi et al: "Enhancement of Cellulose Saccharification Kinetics Using an Ionic Liquid Pretreatment Step" Biotechnology and Bioengineering, Wiley & Sons, Hoboken, NJ, US, vol. 95, No. 5, Dec. 5, 2006, pp. 904-910, XP002470828 ISSN: 0006-35.92, p. 905.
International Search Report and Written Opinion of PCT/EP2008/058044.

* cited by examiner

*Primary Examiner* — Patrick Lewis
*Assistant Examiner* — Everett White
(74) *Attorney, Agent, or Firm* — Minerva Rivero; David P. Owen; Hoyng Monegier LLP

(57) ABSTRACT

A process for converting cellulose to glucose, said process comprising the steps of: providing a hydrated molten salt; contacting the hydrated molten salt with a cellulose-containing material to form dissolved glucose; removing the dissolved glucose from the hydrated molten salt.

25 Claims, 2 Drawing Sheets

PROCESS FOR THE CONVERSION OF CELLULOSE IN HYDRATED MOLTEN SALTS

CROSS-REFERENCES TO RELATED APPLICATIONS

This application is a national phase entry of PCT application number PCT/EP2008/058044, filed on Jun. 24, 2008, which claims priority to U.S. provisional application No. 60/929,373 filed on Oct. 9, 2007, both applications of which are incorporated by reference in their entirety.

BACKGROUND OF THE INVENTION

1. Field of the Invention

The present invention relates to a process for converting cellulose in hydrated molten salts.

2. Description of the Related Art

U.S. Pat. No. 1,943,176 to Graenacher discloses a process for dissolving cellulose in N-ethylpyridinium in the presence of nitrogen-containing bases.

Zhu et al., Green Chem., 2006, 8, 325-327 discloses dissolution of cellulose in a number of ionic liquids, in particular 1-butyl-3-methylimidazolium chloride (BMIMCI) and 1-allyl-3-methylimidazolium chloride (AMIMCI). Microwave heating accelerates the dissolution process. Cellulose can be regenerated from the ionic liquid by addition of water, ethanol, or acetone. The authors suggest the use of ionic liquids for the fractionation of lignocellulosic materials and the preparation of cellulose derivatives and composites.

Swalotski et al. report on the use of ionic liquids, such as BMIMCI, for the preparation of cellulose fibers. See U.S. Pat. No. 6,824,599 B2

U.S. Pat. No. 4,999,149 to Chen discloses a process for high strength cellulose fiber. Dissolving grade cellulose (i.e., cellulose that is substantially lignin free) is dissolved in $ZnCl_2$ at elevated temperature. The cellulose/zinc chloride mixture is extruded into a coagulation medium.

The prior art processes use expensive materials for the ionic liquids. In addition, the disclosed processes do not convert cellulose other than from one form of cellulose to another form of cellulose.

The present invention provides a process for dissolving low-grade cellulose in inexpensive ionic liquids. The present invention further provides a process for purifying cellulose, and a method for converting cellulose, in particular to cellulose fibers.

DESCRIPTION OF ILLUSTRATIVE EMBODIMENTS

The following is a description of certain embodiments of the invention, given by way of example only.

An important aspect of the process of the present invention is the discovery that cellulose may be readily dissolved in hydrated molten salts, which form an inexpensive class of Ionic Liquids. Suitable molten salts include any salt with a melting point below 200° C., in particular hydrates of inorganic salts, the hydrates of $ZnCl_2$ being preferred, $ZnCl_2.4H_2O$ being most preferred. An important aspect of the invention is that the cellulose to be dissolved does not need to be pure. It may contain significant amounts of lignin and/or hemicellulose. Accordingly, inexpensive sources of cellulose may be used.

Another important aspect of the process of the present invention is the discovery that cellulose dissolved in a hydrated molten salt may be converted to glucose simply by heating the solution. Preferably the solution is heated to a temperature of at least 80° C., preferably to a temperature between 100° C. and 150° C. The glucose that is formed is dissolved in the hydrated molten salt.

When the solution is cooled off, the dissolved glucose converts back to cellulose. This property can be used to modify or regenerate cellulose, as has been described in the prior art. An important aspect of the present invention, however, is that the glucose that is formed is separated from the hydrated molten salt. In one aspect the present invention provides a process for converting cellulose to glucose, which can be used as-is in, for example, the food industry, or be reacted further to desirable chemical compounds. An important aspect of the invention is the further conversion of glucose to chemical compounds that are not soluble in the ionic liquid, which allows for their easy removal from the reaction mixture.

Figure 1:
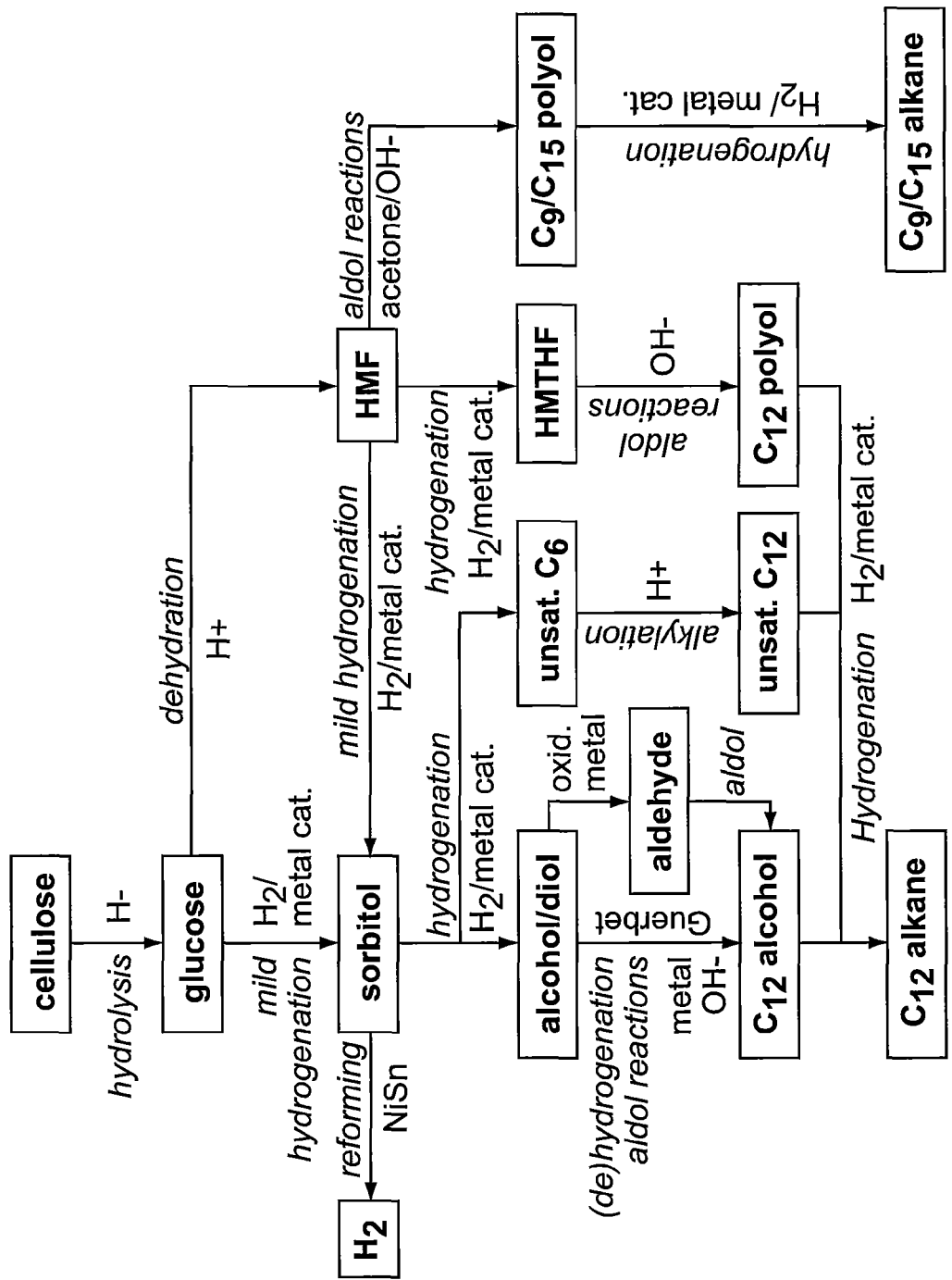
FIG. 1 shows a reaction scheme for the conversion of cellulose.

FIG. 1 shows an overview of reaction paths available for the conversion of glucose to other valuable chemical compounds. For example, glucose may be used as a starting material for the preparation of $C_{12}$ alkane, which is useful as a fuel for internal combustion engines, in particular diesel engines, and as a heating fuel. Or glucose may be used to form mixtures of $C_9/C_{15}$ alkanes.

One way of removing glucose from the hydrated molten salt is by adsorbing the glucose onto a suitable adsorbent. Examples of suitable adsorbents include Sephadex.

Another way of removing glucose from the hydrated molten salt is by flushing the solution with a suitable solvent. The solvent should be immiscible with the hydrated molten salt, and be a good solvent for glucose. Examples of suitable solvents include supercritical carbon dioxide.

The various reaction steps shown in FIG. 1 can be carried out in the ionic liquid medium. For clarification, the term "HMF" stands for hydroxymethyl furfural; the term HMTHF stands for hydroxymethyltetrahydrofuran. The various end products, such as $C_{12}$ alkane and $C_9/C_{12}$ alkane mixture, are insoluble in the ionic liquid. These reaction products can be removed from the reaction mixture by well known standard techniques, such as phase separation and centrifugation. Thus, in one aspect the invention relates to a process comprising the steps of:

a) dissolving cellulose in an ionic liquid;
 b) converting the dissolved cellulose to glucose;
 c) converting the glucose to a reaction product that is insoluble in the ionic liquid.

In a preferred embodiment, the reaction product comprises alkanes, in particular $C_9$, $C_{12}$ and/or $C_{15}$ alkanes.

The dissolution of cellulose in the ionic liquid and the conversion of cellulose to glucose are enhanced by adding an acid to the cellulose/ionic liquid mixture. Examples of suitable acids include mineral acids, in particular HCl.

Step c) may comprise reactions selected from the group consisting of dehydration, hydrogenation, aldol reactions, dehydrogenation, oxidation, alkylation, Guerbet reaction, and combinations thereof.

The term "hydrogenation" as used herein refers to mild hydrogenation, for example carried out by contacting the reactants with hydrogen in the presence of a metal catalyst. A suitable metal catalyst is Raney nickel. Another suitable catalyst is Ru/C.

Aldol reactions are generally carried out in the presence of a base as a catalyst. Suitable bases include hydroxides, in particular alkali metal hydroxides.

Dehydration is catalyzed by Bronstedt acids, in particular inorganic acids, such as HCl.

Alkylation is catalyzed by Lewis or Bronstedt acids.

Figure 2:
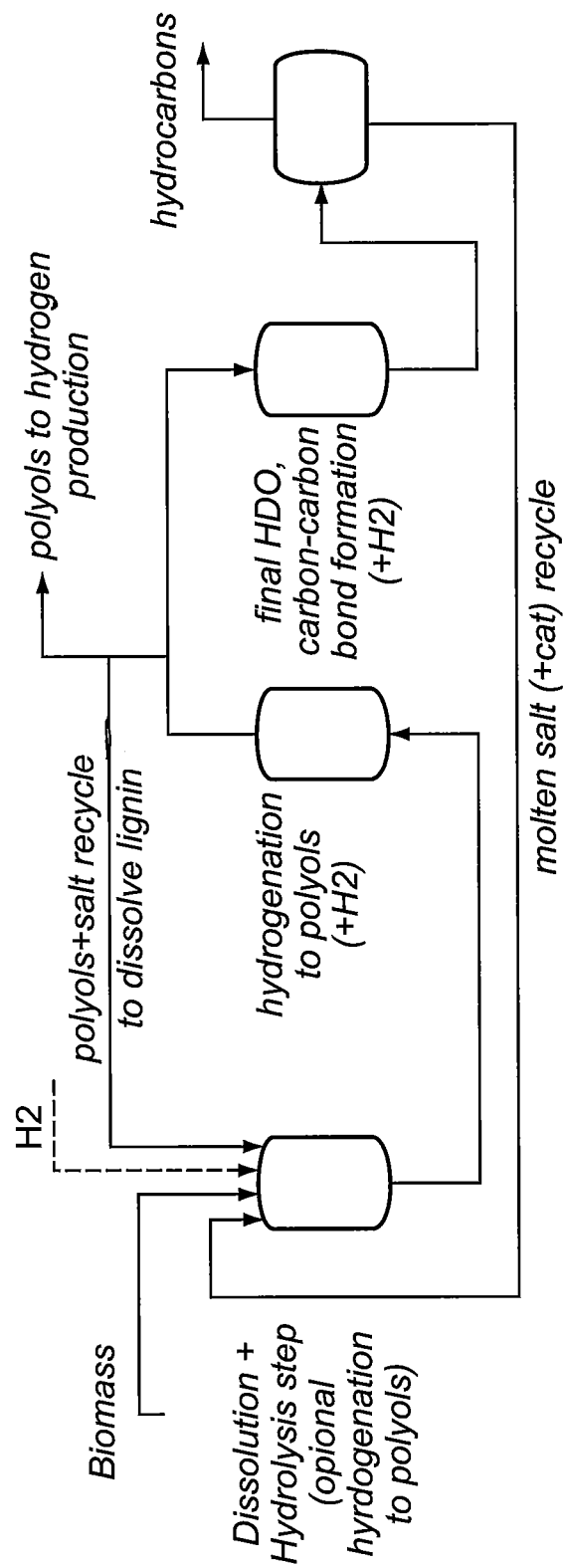
FIG. 2 shows a schematic diagram of a reactor set-up for use in the process of the present invention.

FIG. 2 shows an example of a reactor sequence suitable for a process of the present invention. In the first reactor a (ligno) cellulosic biomass is mixed with a molten salt. Optionally, an acid such as HCl is added to accelerate the conversion of cellulose to glucose. A suitable reaction temperature is in the range of 60 to 120° C. Optionally, hydrogen may be added to the first reactor, as well as Raney nickel catalyst, to commence the hydrogenation of glucose to polyols.

The second reactor is dedicated to the hydrogenation of glucose to polyols, using hydrogen gas in the presence of a hydrogenation catalyst, such as Raney nickel.

In the third reactor a Guerbet reaction takes place. In this reaction the $C_6$ alcohol (e.g., sorbitol) resulting from the hydrogenation of glucose is converted to a $C_{12}$ aldehyde. In a second step the $C_{12}$ aldehyde is reduced to the corresponding $C_{12}$ alcohol.

Finally, in the fourth reactor, the $C_{12}$ alcohol is converted to $C_{12}$ alkane. The $C_{12}$ alkane, being insoluble in the molten salt, is separated from the molten salt. Molten salt, which contains the hydrogenation catalyst, is recycled from the fourth reactor to the first reactor.

As is shown in FIG. 2, part of the polyol product produced in the second reactor may be diverted to produce hydrogen. Hydrogen production may be accomplished by subjecting the polyol (e.g., sorbitol) to a reforming reaction in the presence of a suitable catalyst. Ni/Sn is an example of a suitable catalyst.

Lignin is not soluble in the molten salt medium. Due to its relatively low density it floats to the surface of the first reactor, where it may be removed by skimming. An alternative way of processing is using conventional solid/liquid separation such as filtration.

Another aspect of the invention is the selective dissolution of cellulose in the presence of lignin and/or hemicellulose.

Cellulose is nature's most abundant polymer. Important sources of cellulose include straw, grasses, bagasse, wood, and the similar cellulose-containing forms of biomass material. Almost invariably, cellulose is present in these biomass materials in conjunction with hemicellulose and/or lignin. Processes exist for separating cellulose from hemicellulose and lignin. These processes tend to be expensive, and in many instances involve the use of corrosive or polluting chemicals.

Cotton is an example of a natural source of almost pure cellulose. Cotton is, as a consequence, a valuable material and economically unattractive as a raw material for cellulose-based processes. Algae contain cellulose and little or no lignin. However, the cellulose content of algae is generally modest. As a result, algae are not a major source of cellulose for cellulose-based processes.

The present invention is based on the discovery that cellulose can be selectively liquefied in the presence of lignin. The liquefied cellulose can subsequently be separated from the undissolved lignin. Accordingly, the present invention provides a process for producing a purified and liquefied cellulose from a lignocellulosic biomass material.

In a first step, the present process comprises providing a source of lignocellulose. As discussed hereinabove, nature provides numerous sources of lignocellulosic material. For the sake of convenience reference will be made herein to wood as a lignocellulosic biomass material, but it will be understood that any suitable source of lignocellulosic biomass material may be used.

Saw dust is an attractive starting material for the process of the present invention, because of its small particle size. If wood is available in the form of larger particles, such as wood chips, it is desirable to reduce its particle size. Any available method for particle size reduction is suitable for the purpose of the present invention. Particularly suitable methods include milling, grinding, and shredding.

The particles of lignocellulosic material are mixed with an ionic liquid. Preferred ionic liquids for use in the present process are molten salts, in particular hydrates of inorganic salts. Particularly preferred are the hydrates of zinc chloride, such as $ZnCl2.4H2O$. The invention will be illustrated herein with reference to zinc chloride, but it will be understood that other ionic liquids may be used instead.

In order to dissolve the cellulose component of the lignocellulosic material, it is necessary to heat the wood/zinc chloride mixture to a temperature in the range of from 40 to 200° C. An acid may be added in order to increase the solubility of the cellulose component. Strong mineral acids are preferred for use herein, with HCl being particularly preferred for reasons of cost, compatibility, and ease of removal.

In general, sources of lignocellulosic material comprise significant amounts of water. Even "dry" wood contains 5 wt % water or more. The water is freed up as the cellulose dissolves, and becomes part of the mixture. In addition, the dissolution of cellulose in the ionic liquid involves the destruction of hydrogen bonds between cellulose polymer chains by abstraction of water molecules. In other words, the dissolution process itself produces water.

In order for the ionic liquid to retain its solvent strength it may be necessary to remove water from the mixture. For this reason it may be desirable to operate at a temperature above 100° C., so that water is readily removed by evaporation.

It has been found that higher temperatures and the presence of acid promote the conversion of dissolved cellulose to glucose. Therefore, it may be desirable to operate at a temperature of more than 80° C., preferably more than 100° C., in the presence of an acid, if conversion of cellulose is desired. The amount of acid may be relative small, typically less than 1 wt %, generally in the range of from 0.1 to 0.8 wt %.

In a specific embodiment of the invention, the dissolved cellulose is used for the production of formed products, such as cellulose sheets, cellulose films, and cellulose fibers. For purposes of this embodiment it is important to avoid depolymerization of the cellulose, and the formation of glucose (which is the ultimate form of depolymerization) is undesirable in this context. In general, glucose formation can be avoided by operating at a temperature in the range of from 40 to 80° C., preferably in the range of from 60 to 70° C.

The skilled person will appreciate that the dissolution rate decreases as lower mixing temperatures are employed. If the mixing temperature is at the low end of the range, i.e., less than 60° C., it may be desirable to add acid to the mixture in order to increase the dissolution rate to an acceptable level. It has been found that the use of acid at these lower temperatures does not result in an unacceptably high conversion of the cellulose to glucose.

In order to remove water while operating at temperatures below 100° C. it may be desirable to operate under reduced pressure. In general, the optimum pressure is near the saturated vapor pressure of water at the operating temperature. This allows the water to readily evaporate, without causing violent boiling of the mixture. By way of example, the saturated steam pressure at 65° C. is 0.25 bar. It is desirable to operate the dissolution step at a reduced pressure of 0.25 bar if the selected dissolution temperature is 65° C.

Lignin, which is the other main component of lignocellulosic biomass material, does not dissolve in the ionic liquid under the above-defined conditions. After the cellulose is fully dissolved the remaining lignin may be removed by any known technique for separating solid particles from a liquid. Examples of suitable techniques include filtration, settling, centrifugation, and the like. Care should be taken that the temperature of the mixture is maintained during the lignin-removal step, to avoid precipitation of previously dissolved cellulose (if the temperature were allowed to drop), or depolymerization of the dissolved cellulose (if the temperature were allowed to rise).

Lignin recovered from this separation step is a valuable raw material for the production of specialty chemicals.

In many cases the lignocellulosic biomass material further comprises hemicellulose. It is, in general, desirable to avoid contamination of the cellulose with hemicellulose if the cellulose is used for making formed products, such as fibers or sheets. The presence of significant quantities of hemicellulose decreases the mechanical strength of the fiber or sheet.

Being less stable than cellulose, hemicellulose dissolves much faster than cellulose. Moreover, hemicellulose is converted to, among others, xylose under the conditions of the mixing step. Having a far greater solubility than cellulose, xylose can be readily removed from the mixture by any one of the techniques known to the skilled person. An example of a particularly suitable technique is solvent extraction with, for example, a polar solvent such as an alcohol or water. Also conventional solid/liquid separation techniques can be used such as filtration.

The cellulose may be recovered from the solution by extruding the solution into a coagulating medium. Examples of a suitable coagulating medium include the $C_1$ to $C_8$ alcohols and ketones, in particular the alcohols of the group of straight chain and branched chain $C_1$ to $C_4$ alcohols, such as methanol, ethanol, propanol, and iso-propanol. Particularly suitable ketones include the $C_3$ to $C_5$ ketones such as acetone and methylethylketone (MEK).

The cellulose may be formed into fibers by extruding the solution into the coagulating medium through an orifice having a plurality of small extrusion holes, such as a spinneret. In general, the extruded fibers are not fully crystallized. Crystallization may be enhanced by one or more of the following post-treatment steps.

The fibers are removed from the coagulating medium. Preferably, residual coagulating medium is removed, for example by evaporation. The fibers may be stretched by applying tension to the fibers. The stretching action acts to orient the polymer molecules in the fibers.

Subsequently the fibers may be submerged in a bath containing water.

Thus, the invention has been described by reference to certain embodiments discussed above. It will be recognized that these embodiments are susceptible to various modifications and alternative forms well known to those of skill in the art.

The invention claimed is:

1. A process for converting lignocellulosic biomass material to xylose and glucose, said process comprising the steps of:
   a) providing an inorganic hydrated molten salt consisting essentially of a hydrate of zinc chloride;
   b) contacting the hydrated molten salt with a lignocellulosic biomass material containing at least 5 wt % water and containing cellulose and hemicellulose, to form dissolved xylose;
   c) removing the dissolved xylose;
   d) continuing to contact the hydrated molten salt with the treated lignocellulose biomass from step b);
   e) removing the dissolved glucose from the hydrated molten salt.

2. The process of claim 1 wherein step c) and e) comprises flushing the hydrated molten salt with a solvent.

3. The process of claim 2 wherein the solvent is selected from the group consisting of organic solvents, supercritical fluids, and mixtures thereof.

4. The process of claim 1 wherein the dissolved glucose and/or xylose is removed by conversion to a material that is poorly soluble in the hydrated molten salt.

5. The process of claim 4 wherein the glucose and/or xylose is converted to a material comprising an alcohol.

6. The process of claim 5 wherein the glucose and/or xylose is converted to a material comprising an alcohol by a process comprising mild hydrogenation.

7. The process of claim 5 wherein the glucose and/or xylose is converted to a material comprising an alcohol by a process comprising selective oxidation.

8. The process of claim 5 comprising the further step of hydrogenating the alcohol to form an alkane.

9. The process of claim 8 wherein the alcohol is separated from the hydrated molten salt prior to conversion to the alkane.

10. The process of claim 8 wherein hydrogen used in the hydrogenation reaction is generated by reforming cellulosic biomass.

11. The process of claim 8 wherein hydrogen used in the hydrogenation reaction is generated by reforming lignin.

12. The process of claim 4 wherein the conversion is carried out electrochemically.

13. The process of claim 4 wherein the conversion is carried out under the addition of microwave energy.

14. The process of claim 4 wherein the conversion is carried out under the addition of ultrasound energy.

15. The process of claim 4 wherein the conversion is catalyzed in the presence of a catalyst.

16. The process of claim 15 wherein the catalyst is a particulate solid material that is dispersed in the hydrated molten salt.

17. The process of claim 4 wherein the conversion comprises a reaction in a micro channel reactor.

18. The process of claim 17 wherein the micro channel reactor is at least partially coated with a catalytic material.

19. The process of claim 4 wherein the reaction conditions comprise a temperature of from 40 to 80° C.

20. The process of claim 19 wherein the reaction conditions comprise the substantial absence of mineral acid.

21. The process of claim 19 whereby water is removed from the inorganic hydrated salt during step b) and step d).

22. The process of claim 21 whereby step b) and step d) are carried out under reduced pressure.

23. The process of claim 22 whereby step b) and d) are carried out at a pressure which is at or near the saturated steam pressure of the reaction temperature.

24. The process of claim 23 whereby step b) and d) are carried out at a temperature in the range of 60 to 70° C. and a pressure in the range of 0.20 to 0.30 bar.

25. The process of claim 19 whereby lignin is removed from the molten salt during or after step d).

* * * * *